US008399021B2

(12) United States Patent
Delaite et al.

(10) Patent No.: US 8,399,021 B2
(45) Date of Patent: Mar. 19, 2013

(54) PREPARATION OF POLY(ETHYLENE OXIDE)-COATED NANOPARTICLES OF MAGHEMITE

(75) Inventors: Christelle Delaite, Froeningen (FR); Christophe Flesch, Rixhein (FR); Philippe Dumas, Fraize (FR)

(73) Assignees: Centre National de la Recherche Scientifique (C.N.R.S.), Paris (FR); Universite de Haute Alsace, Mulhouse (FR)

( * ) Notice: Subject to any disclaimer, the term of this patent is extended or adjusted under 35 U.S.C. 154(b) by 830 days.

(21) Appl. No.: 12/278,594

(22) PCT Filed: Feb. 7, 2007

(86) PCT No.: PCT/FR2007/000223
§ 371 (c)(1), (2), (4) Date: May 21, 2009

(87) PCT Pub. No.: WO2007/090962
PCT Pub. Date: Aug. 16, 2007

(65) Prior Publication Data
US 2010/0015059 A1    Jan. 21, 2010

(30) Foreign Application Priority Data
Feb. 7, 2006   (FR) .................................... 06 01076

(51) Int. Cl.
*A61K 9/14*   (2006.01)
(52) U.S. Cl. ...................................... 424/489
(58) Field of Classification Search .................. None
See application file for complete search history.

(56) References Cited

U.S. PATENT DOCUMENTS

| 5,916,539 A | 6/1999 | Pilgrimm |
| 2006/0018835 A1 | 1/2006 | Lucien et al. |
| 2007/0090323 A1 | 4/2007 | Duguet et al. |

FOREIGN PATENT DOCUMENTS

FR      2 855 315      12/2004

OTHER PUBLICATIONS

Hu et al, Cellular Response to Magnetic Nanoparticles "PEGylated" via Surface-Initiated Transfer Radical Polymerization, Biomacromolecules, 2006, 7, 809-816.*
Flesch et al., "Poly(ethylene glycol) Surface Coated Magnetic Particles," Macromol. Rapid Comm., vol. 26, No. 9, pp. 1494-1498 (Jun. 9, 2005).
Aoyama et al., "Adsorption of silane coupling agent on Co-gamma-$Fe_2O_3$ and its effect on dispersibility," J. of Mat. Sci., vol. 23, pp. 1729-1734 (1988).

* cited by examiner

*Primary Examiner* — Paul Dickinson
(74) *Attorney, Agent, or Firm* — Young & Thompson

(57) ABSTRACT

The invention relates to a material consisting of an aqueous dispersion of PEG-coated nanoparticles of maghemite. The process for preparing said material consists in polymerizing ethylene oxide in the presence of nanoparticles of maghemite in an aqueous dispersion. The polymerization is initiated using reactive groups which are capable of initiating the polymerization of ethylene oxide without the addition of a catalyst, and which are attached to the nanoparticles of maghemite by means of a coupling agent comprising an alkoxysilyl group and one or more of said reactive groups. Applications: contrast agent for MRI.

12 Claims, 3 Drawing Sheets

PREPARATION OF POLY(ETHYLENE OXIDE)-COATED NANOPARTICLES OF MAGHEMITE

FIELD OF THE INVENTION

Figure 1:
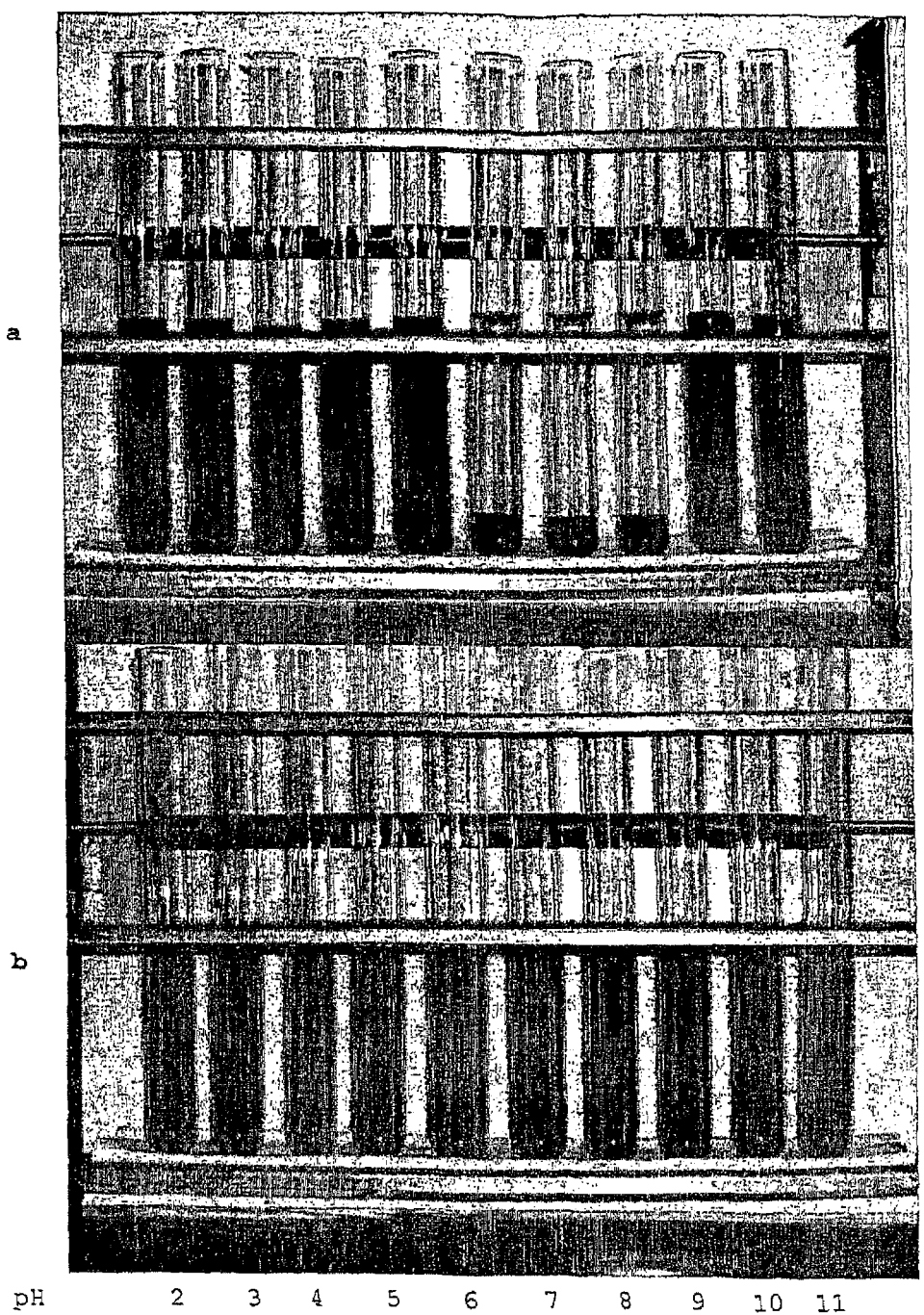

The present invention relates to nanoparticles comprising a maghemite core and a shell of polyethylene oxide, as well as a method of preparation thereof.

BACKGROUND OF THE INVENTION

Certain medical treatments involve the injection of particles into the blood of a patient. This is the case in particular for MRI contrast agents. The same will apply in the future to mediators for magnetic hyperthermia. The particles are generally injected in the form of colloidal dispersions, and it is necessary for these dispersions to be stable.

A dispersion can be stabilised either by electrostatic repulsion or by steric repulsion.

A dispersion stabilised by electrostatic repulsion cannot be used for an injection, because the charged particles would be eliminated immediately by the immune system. Furthermore, iron oxide has an isoelectric point (pH value for which the surface charge density is zero) of 7. Thus under physiological pH conditions the iron oxide nanoparticles are not charged and are therefore precipitated.

A dispersion stabilised by steric repulsion is obtained in particular by grafting of hydrophilic macromolecules on the surface of the particles.

Iron oxide particles are known which are coated with a layer of hydrophilic polymer, such as dextran. These particles are used for MRI scanning of the liver or lymphatic ganglions. They are generally designated by (U)SPIO [(Ultrasmall) SuperParamagnetic Iron Oxide] and they are described in particular by Neuberger et al [J. Magn. Magn. Mat., 293 (2005) 483]. They are prepared by coprecipitation of iron oxide directly in an aqueous solution of the preformed polymer as described in U.S. Pat. No. 4,452,773. In these materials there is no covalent bond between the maghemite and the polymer. The polymer coating is therefore sensitive to phenomena of desorption/depletion. In order to improve the quality of these particles, it has been proposed to cross-link the dextran around the nanoparticles (U.S. Pat. No. 5,262,176) or to cross-link the dextran by means of iron oxide nanoparticles previously modified at the surface by an aminosilane-type derivative (FR-2,855,315). The principal drawback of these methods according to the prior art is the number of steps in the chemical modification and the fact that each modification step necessitates a very long purification step since it is essentially effected by dialysis. Furthermore, dextran is not very effective for limiting the adsorption of plasma proteins and therefore extending the half-life of the nanoparticles.

It is known that polyethylene oxide PEO is an effective surfactant for increasing the plasma half-life of particles, in particular when it is in telechelic form, for example a polyethylene glycol PEG. However, the grafting ratio of PEO on the surface of the nanoparticles is poor. Indeed, the steric hindrance resulting of the polymer chains around a particle limits the quantity of polymer which is fixed on the particle due to the fact that access to the active sites of the particle surface is limited. For example, Butterworth et al, [Surf. A, 179, 93 (2001)], describe such particles for which the maximum PEG content is 9% by mass. Furthermore, Davis et al, [Coll Surf A: Physicochem. Eng. Aspects, 179 (2001) 93], describe the grafting onto magnetic oxide particles of polyethylene oxide (PEO) chains which are preformed and functionalised by an organosilane group. This technique exhibits the same drawbacks as the one described by Butterworth as mentioned above. Furthermore, the preformed chains are generally obtained by a method using a catalyst and they contain residues of this catalyst which may be toxic for medical applications of the modified particles.

SUMMARY OF THE INVENTION

The object of the present invention is to provide a simpler method without a catalyst for grafting macromolecules on the surface of maghemite nanoparticles, achieving a substantial grafting ratio, in order to obtain nanoparticles which have a polymer coating fixed by covalent (and therefore stable) bonding on a maghemite core and which are devoid of toxic residues.

Consequently, the present invention relates to a method of preparation of a material comprising a n aqueous dispersion of maghemite nanoparticles coated with polyethylene glycol PEG, as well as the material obtained.

DETAILED DESCRIPTION OF THE INVENTION

The method according to the present invention consists in polymerising ethylene oxide in the presence of maghemite nanoparticles in an aqueous dispersion, and it is characterised in that the polymerisation is initiated using reactive groups R which are capable of initiating the polymerisation of ethylene oxide without the addition of a catalyst and which are fixed on the maghemite nanoparticles by means of a coupling agent comprising an alkoxysilyl group and one or more groups R.

More precisely, the method consists in:
preparing an aqueous dispersion of maghemite nanoparticles;
modifying the maghemite nanoparticles in dispersion by a coupling agent chosen from amongst the alkoxysilanes bearing at least one group R;
polymerising ethylene oxide in the presence of the silylated maghemite nanoparticles obtained in the preceding step.

A coupling agent which can be used in the method according to the present invention is an alkoxysilane, in particular a mono-, di- or preferably a trialkoxysilane comprising at least one group R which makes it possible to initiate the polymerisation of ethylene oxide.

The group R is preferably a hydroxyl group or a hydroxyl group precursor. The epoxide group may be mentioned as an example of a hydroxyl group precursor.

The alkyl groups of a coupling agent preferably have 1 to 4 carbon atoms, and more preferably 1 to 2 carbon atoms. The alkoxy groups of a coupling agent may be identical or different.

The modification of the maghemite nanoparticles is carried out in an aqueous solvent or in an organic solvent. When an anhydrous organic solvent is used, it is preferably chosen from amongst the polar aprotic solvents, for example DMF. When the solvent is not anhydrous, it can be chosen from amongst the protic solvents, for example ethanol.

As examples of coupling agents mention may be made of compounds of the hydroxysilane type in which R is OH, for example hydroxymethyltriethoxysilane, N-(hydroxyethyl)-N-methylaminopropyl-trimethoxysilane and bis(2-hydroxyethyl)-3-aminopropyl-triethoxysilane. Mention may also be made of compounds of the glycidoxypropylsilane type in which the substituent R is an epoxide group, for example 3-(glycidoxypropyl)trimethoxysilane, (3-glycidoxypropyl)- dimethylethoxysilane, (3-glycidoxypropyl)methyldiethoxysilane, and (3-glycidoxypropyl)methyldimethoxysilane.

The maghemite dispersion can be prepared by methods described in the prior art.

For example a method as described by R. Massart (IEEE Transactions on Magnetics, Vol. MAG-17, N° 2, March 1981) consists in preparing an aqueous solution of $FeCl_3$ and of $FeCl_2$ acidified by HCl, adding this solution to an aqueous ammonia solution, separating out the formed precipitate without washing by centrifugation or by decantation. Then the precipitate is:
- either brought into contact with an aqueous solution of tetramethylammonium hydroxide,
- or brought into contact with an aqueous perchloric acid solution, then isolated by centrifugation.

The isolated nanoparticles are then redispersed in water, preferably in a quantity such that the concentration of maghemite nanoparticles in the water is between 5 and 10% by mass.

Another method of preparation of maghemite nanoparticles is described by S. Mornet et al [J. Magn. Mat, 293 (2005) 127]. It consists in (1) precipitating magnetite nanoparticles in an aqueous solution by adding an aqueous solution of $FeCl_2$ acidified by HCl to an aqueous solution of $FeCl_3$, then adding ammonia, whilst agitating, (2) eliminating the supernatant after the formation of the precipitate, (3) partially oxidising the precipitate formed to maghemite by rapid addition of nitric acid, (4) totally oxidising by addition of a hot iron nitrate solution, then washing the solid obtained by centrifugation/redispersion cycles and (5) peptising by addition of nitric acid.

In a particular embodiment, the step of modification of the nanoparticles comprises the following phases:
- mixing, whilst agitating, of an aqueous maghemite dispersion and a solution of coupling agent at a temperature between 20 and 100° C. for a duration of between 3 and 20 hours;
- hydrolysis of the alkoxy groups of the coupling agent and of the precursor of the reactive group R, as the case may be;
- extraction of the nanoparticles by centrifugation;
- drying under a dynamic vacuum at a temperature between 20 and 150° C. for a duration of between 3 and 24 hours.

In a particular embodiment, the step of fixing of PEO chains on the nanoparticles modified by the coupling agent is carried out under an inert atmosphere in an apolar anhydrous solvent, and it comprises the following phases:
- introduction into a reactor of an apolar anhydrous solvent and maghemite nanoparticles modified by the coupling agent then treated in order to render them anhydrous;
- progressive addition of ethylene oxide under a partial vacuum and whilst agitating, the reactor being maintained at a temperature of −35° C. to −10° C. for a duration of 15 to 30 minutes;
- maintaining the reaction mixture for a duration of between 10 and 100 hours at a temperature between 40 and 100° C. (for example 90° C. for 50 hours),
- extraction of the nanoparticles by centrifugation and washing, then dispersion in water.

The apolar anhydrous solvent is advantageously toluene.

The material obtained by the method according to the invention is an aqueous dispersion of aggregates of elementary nanoparticles, and it is characterised in that:
- an elementary nanoparticle comprises a maghemite core and a PEO coating;
- the maghemite core comprises an aggregate of maghemite nanoparticles having a diameter of 7 to 10 nm, measured by transmission electron microscopy;
- the maghemite core has a diameter of 40 to 50 nm, measured by dynamic diffusion of light;
- the aggregates of elementary nanoparticles have a diameter of 50 nm to 90 nm, measured by dynamic diffusion of light;
- the ratio by weight of PEO/maghemite in the aggregates of elementary nanoparticles is 80 to 850 mg/g corresponding to a ratio by weight of PEO/aggregates of 7 to 46% by weight.

A dispersion forming the material according to the present invention can be used advantageously as a contrast agent in particular for MRI scanning.

The present invention is explained in greater detail by the following example, which is given by way of illustration and to which the invention is not limited.

EXAMPLE

Preparation of a Maghemite Dispersion

In each of the steps of the method of preparation of the maghemite dispersion, the water used is HPLC-quality ultra-pure water in order to avoid the presence of flocculent ions.

In the course of a first step a magnetite precipitate is formed according to the following mode of operation. An aqueous solution of $FeCl_3$ is prepared by introducing, whilst agitating (500 rpm), 10.87 g of $FeCl_3$ (0.039 mol) in a 1 L reactor equipped with mechanical agitating means and a reflux, and containing 435 mL of water at 80° C. When $FeCl_3$ is totally dissolved, a solution of 3.92 g of $FeCl_2$ (0.0195 mol) previously dissolved in 22 mL of HCl 1.5 M is added, and the mixture is agitated until the colour is uniform. The agitating speed is then increased to 850 rpm and 45 mL of ammonia are added very quickly to the reaction medium. A black magnetite precipitate is formed instantly. The reaction medium is left whilst agitating for 15 min, then it is extracted from the reactor and is left to decant into a beaker placed on a magnetic plate. Then the supernatant is eliminated by aspiration as the majority of liquid is removed, whilst the magnetite nanoparticles obtained are kept shielded from the air.

In the course of a second step a partial oxidation of the magnetite is carried out to form maghemite, and the exchange of the counter-ions $NH_4^+$ by $NO_3^-$ according to the following mode of operation. At ambient temperature, add 70 mL of nitric acid (2 M), agitate for 2 to 3 minutes then leave to decant for 10 minutes. Eliminate the supernatant. Since iron oxide dissolves in these conditions of acidity, it is necessary to carry out this step as rapidly as possible in order to limit losses.

In the course of a third step a total oxidation is carried out according to the following mode of operation. An oxidising solution of iron nitrate (0.33 M) is prepared by dissolving 10 g of iron nitrate in 75 mL of water heated to 100° C. The hot solution is poured onto the maghemite and it is kept at 100° C. for 30 minutes. Then the heating is stopped and the solution is left to cool and decant. The solid matter is washed in acetone in the course of three centrifugation-redispersion cycles (8400 $rpm^{-1}$, 2 minutes) in order to eliminate the residual chloride and nitrate ions.

In the course of a fourth step a peptisation of the solid matter is carried out according to the following mode of operation. 50 mL of nitric acid (2 M) are added to the solid matter obtained at the end of the previous step, agitation is carried out for 15 minutes followed by centrifugation. After the centrifugation the supernatant is eliminated and again 3 washing operations are carried out with acetone. Then the maghemite is redispersed in 60 mL of water and the traces of acetone are removed with the Rotovapor at 80° C. until the elimination of water starts. Then the ferrofluid obtained is decanted into a 60 mL phial and is made up with water. The dispersion is treated for 3 minutes by an ultrasound probe to disintegrate the nanoparticles to the maximum extent.

The characteristics of the maghemite dispersion thus obtained are set out in Table I below.

TABLE I

| Parameter | Analytical technique | Result |
|---|---|---|
| Maghemite concentration | Volume dosing | 79 g/L |
| Isoelectric point | Zetametry | 6.5 |
| Flocculation range | Visual | 5 < pH < 9 |
| Concentration of Cl⁻ ions resulting in flocculation | Visible spectrophotometry | 0.05 M of NaCl at pH 4.5 |
| Natural pH | pH meter | 2.5 |
| Size of the nanoparticles | Transmission electron microscopy | 11 ± 3 nm |
|  | Dynamic diffusion of light | 38 ± 5 nm at pH 5 |
| Specific surface area | Adsorption of nitrogen (BET) | 130 m²/g |
| Magnetisation | SQUID* magnetometer | 49 emu/g at 5000 Oe |

*Superconducting Quantum Interference Device

Modification of Maghemite Nanoparticles in Dispersion

In the course of a first step, the epoxy group of 3-(glycidoxypropyl)trimethoxysilane was hydrolysed in 50 mL of water acidified at pH 2 with the aid of a sulphuric acid solution (0.05 M), according to the following mode of operation. In a flask topped by a coolant, the silane (2.22 g, 9.2 mmol) and the acid solution were heated under reflux conditions with the aid of an oil bath for one hour. After cooling, the pH of the medium was adjusted to 5 by the addition of a sodium acetate solution (0.5 M). At the same time 20 g of ferrofluid (corresponding to 1.7 g of maghemite) are also adjusted to pH 5, then added to the silane solution. The dispersion is then brought to reflux for 3.5 hours. After cooling, the dispersion is centrifuged (20 minutes, 8400 rpm$^{-1}$) and the excess of silane is eliminated by five centrifugation-dispersion cycles in water. The silylated maghemite is finally dried under a dynamic vacuum at 70° C. for 24 hours, this latter step causing the formation of covalent bonds between the silane and the maghemite.

The quantity of silane immobilised on the surface of the maghemite nanoparticles, determined by thermogravimetric analysis, is 0.5 mmol/g of maghemite.

Fixing of Polymer Chains 0.5 g of modified maghemite were introduced into a 500 mL flask and treated under a dynamic vacuum at 130° C. for 3 hours. Then 160 mL of dry toluene were added under a stream of nitrogen and an ampoule containing liquefied ethylene oxide (EO) is fixed on the flask. The maghemite dispersion in toluene is cooled with the aid of a cold bath (composed of an ethanol/isopropanol mixture cooled with liquid nitrogen) in order to put the device under a static vacuum with the aid of a vane pump. The EO (10 mL, 0.2 mmol) is then added progressively in order to avoid excess pressures in the device, and the reaction medium kept in the cold bath is agitated for 30 minutes. Then heating is carried out at 50° C. with the aid of an oil bath for 95 hours. After reaction the dispersion is centrifuged and the solid matter is washed in turn 3 times with water, 3 times with THF and 3 times with methanol. The centrifugation tubes are heated by hot air in order to facilitate the redispersion of the solid matter. A portion of the solid matter is then dispersed in water and another portion is dried under a dynamic vacuum at ambient temperature for 24 hours.

The characteristics of the nanocomposites obtained are set out in Table II below.

TABLE II

| Parameter | Analytical technique | Result |
|---|---|---|
| Polymer content | Thermogravimetry | 850 mg/g of maghemite |
| Isoelectric point | Zetametry | none |
| Flocculation range | Visual | none |
| Concentration of ions Cl⁻ resulting in flocculation | Visible spectrophotometry | Stable in the range studied up to 1 M |
| Size of the nanoparticles | Dynamic diffusion of light | 52 ± 6 nm at pH 5 |
| Magnetisation | SQUID magnetometer | 26 emu/g at 5000 Oe |

FIG. 1 shows the behaviour as a function of the pH of a non-modified maghemite dispersion (upper portion a) and of the maghemite dispersion modified by grafting of PEO prepared in the present example (lower portion b). It appears that the non-modified maghemite nanoparticles flocculate in the pH range from 7 to 9, whilst the modified nanoparticles remain stable.

Figure 2:
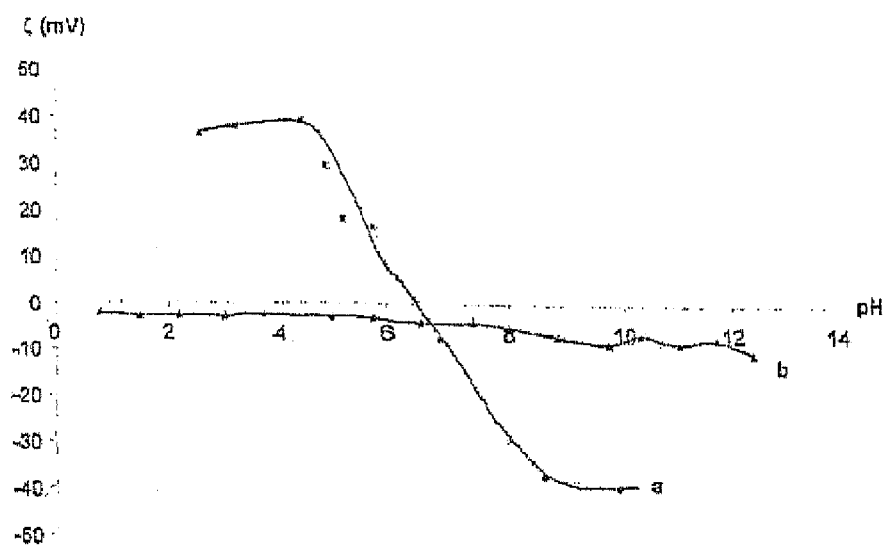

FIG. 2 shows the development of the zeta potential ξ as a function of the pH of the dispersion of modified nanoparticles [curve a) for the untreated maghemite, curve b) for the maghemite grafted by the PEO]. The absence of an isoelectric point and the low value of the zeta potential irrespective of the pH confirm the steric nature of the stabilisation. The value of the potential is −4.5 mV at pH 7.4, which is the pH of blood.

Figure 3:
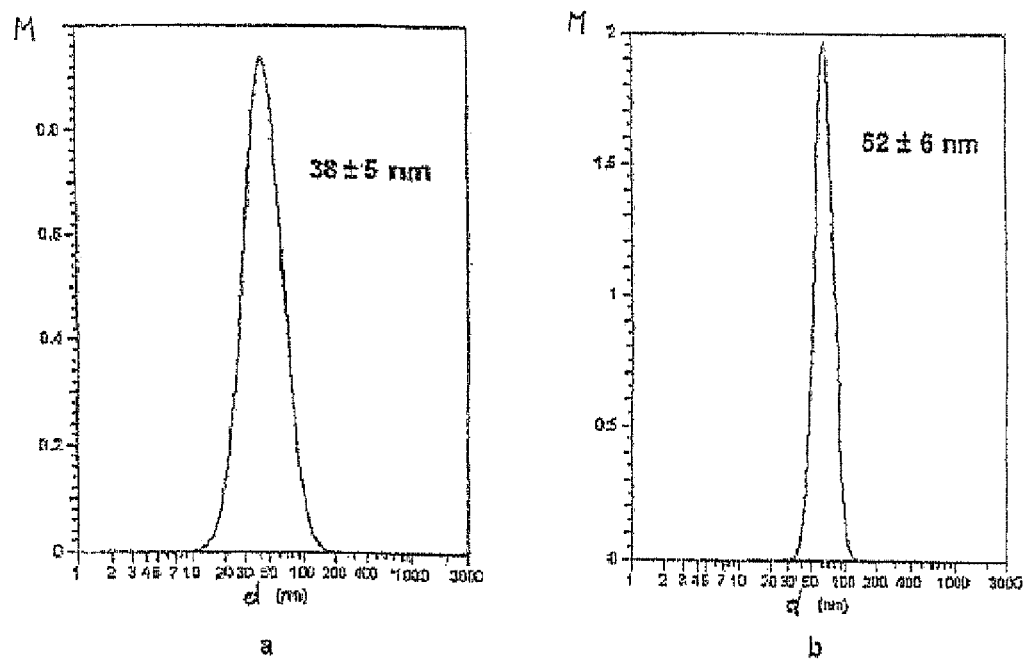

FIG. 3 shows the mean size distribution. The proportion M is shown on the Y axis, the dimension d (in nm) is shown on the X axis. The curve a) corresponds to the non-modified maghemite nanoparticles dispersed in distilled water, at their natural pH, and therefore stabilised by electrostatic means. The curve b) corresponds to the modified maghemite dispersion obtained in the present example.

It appears that the sizes remain small after grafting of PEO.

Figure 4:
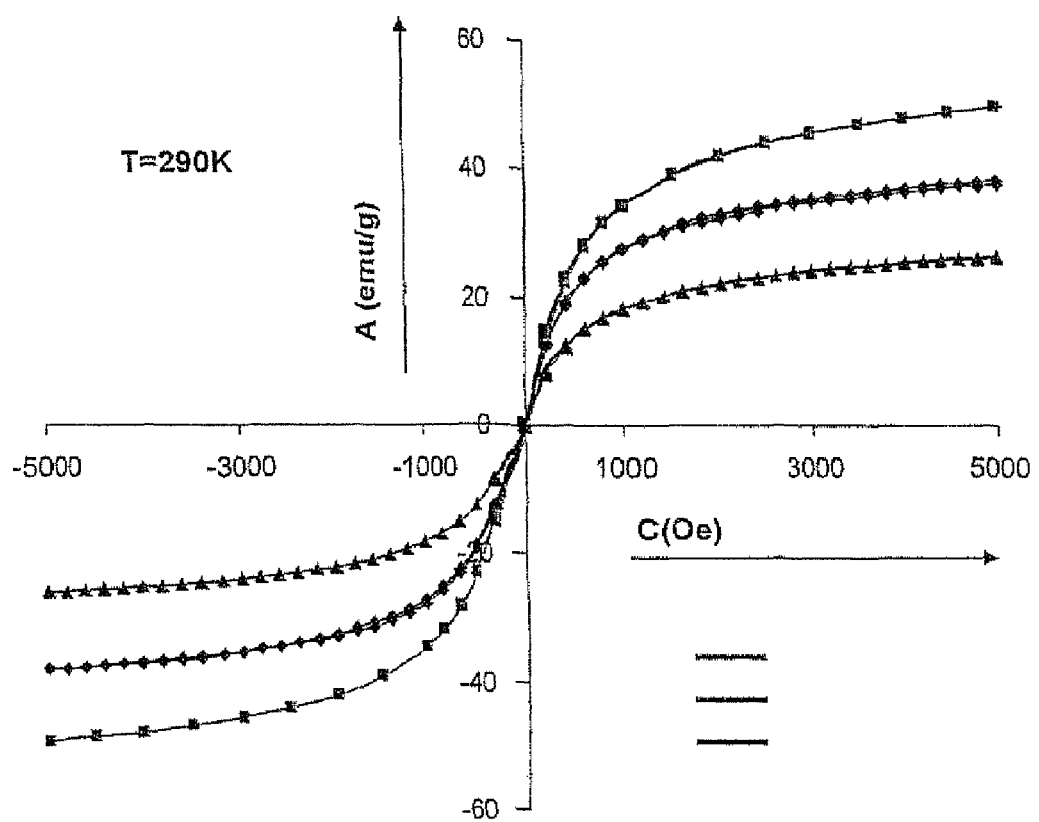

FIG. 4 shows the magnetisation as a function of the magnetic field of non-modified maghemite (curve shown by ■), of maghemite modified by silane (curve shown by ♦) and of maghemite modified by PEO (curve shown by ▲). On these curves the magnetic field C (in oerstedt) is shown on the X axis and the magnetisation A (emu/g) is shown on the Y axis. The absence of hysteresis confirms that maghemite modified by PEO exhibits superparamagnetic behaviour at ambient temperature.

The invention claimed is:

1. A method of preparing an aqueous dispersion of maghemite nanoparticles coated with polyethylene oxide (PEO), the method comprising:

preparing modified maghemite nanoparticles by modifying maghemite nanoparticles with a coupling agent comprising an alkoxysilyl group and at least one reactive R group, the reactive R group capable of initiating polymerisation of ethylene oxide to polyethylene oxide in the absence of an additional catalyst;

adding ethylene oxide to said modified maghemite nanoparticles under anhydrous conditions;

polymerizing the ethylene oxide in the presence of said modified maghemite nanoparticles to prepare PEO-coated nanoparticles; and dispersing the PEO-coated nanoparticles in an aqueous solution.

2. The method according to claim 1, wherein preparing modified maghemite nanoparticles comprises:
- preparing an aqueous dispersion of maghemite nanoparticles; and
- adding the coupling agent to the aqueous dispersion of maghemite nonoparticles.

3. The method according to claim 1, wherein the at least one reactive R group is a hydroxyl group or a hydroxyl group precursor.

4. The method according to claim 1, wherein the alkoxysilyl group comprises alkyl groups having 1 to 4 carbon atoms.

5. The method according to claim 3, wherein the alkoxysilyl group comprises alkyl groups having 1 to 4 carbon atoms.

6. The method according to claim 1, wherein the alkoxysilyl group is a trialkoxysilyl group.

7. The method according to claim 2, wherein the alkoxysilyl group is a trialkoxysilyl group.

8. The method according to claim 3, wherein the alkoxysilyl group is a trialkoxysilyl group.

9. The method according to claim 1, wherein preparing the modified maghemite nanoparticles comprises:
- preparing a dispersion of maghemite nanoparticles in an organic solvent; and
- adding the coupling agent to the organic dispersion of maghemite nanoparticles.

10. The method according to claim 1, comprising:
- introducing into a reactor the modified maghemite nanoparticles and an apolar anhydrous solvent under an inert atmosphere;
- progressively adding the ethylene oxide to the reactor under a partial vacuum while agitating, the reactor being maintained at a temperature between −35° C. to −10° C. for a duration of 15 to 30 minutes, to produce a reaction mixture;
- maintaining the reaction mixture for a duration of between 10 hours and 100 hours at a temperature between 40° C. and 100° C., to prepare PEO-coated nanoparticles; and
- extracting the PEO-coated nanoparticles by Centrifugation, washing the nanoparticles, and then dispersing the nanoparticles in water.

11. The method according to claim 1, wherein preparing modified maghemite nanoparticles comprises:
- preparing an aqueous dispersion of maghemite nanoparticles;
- adding the coupling agent to the aqueous dispersion of maghemite nanoparticles;
- modifying the maghemite nanoparticles with said coupling agent by hydrolysing the alkoxy groups and the R groups of the coupling agent; and
- extracting and drying the modified nanoparticles.

12. The method according to claim 1, wherein preparing the modified maghemite nanoparticles comprises:
- preparing a dispersion of maghemite nanoparticles in an organic solvent;
- adding the coupling agent to the organic dispersion of maghemite nanoparticles;
- modifying the maghemite nanoparticles with said coupling agent by hydrolysing the alkoxy groups and the R groups of the coupling agent; and
- extracting and drying the modified nanoparticles.

\* \* \* \* \*

UNITED STATES PATENT AND TRADEMARK OFFICE
CERTIFICATE OF CORRECTION

PATENT NO. : 8,399,021 B2  Page 1 of 1
APPLICATION NO. : 12/278594
DATED : March 19, 2013
INVENTOR(S) : Delaite et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1118 days.

Signed and Sealed this
First Day of September, 2015

Michelle K. Lee
*Director of the United States Patent and Trademark Office*